United States Patent [19]

Schnatterer et al.

[11] Patent Number: 5,773,664
[45] Date of Patent: Jun. 30, 1998

[54] PROCESS FOR THE RECOVERY OF 4-HYDROXYBENZALDEHYDE FROM REACTION MIXTURES CONTAINING SAME

[75] Inventors: Albert Schnatterer; Helmut Fiege, both of Leverkusen; Frank Jelitto, Bergisch Gladbach; Peter Skornia, Bonn; Karl-Heinz Theisen, Köln, all of Germany

[73] Assignee: Bayer Aktiengesellschaft, Leverkusen, Germany

[21] Appl. No.: 592,162

[22] Filed: Jan. 26, 1996

[30] Foreign Application Priority Data

Feb. 1, 1995 [DE] Germany ................... 195 03 163.6

[51] Int. Cl.⁶ ................... C07C 45/78; C07C 45/81
[52] U.S. Cl. ................... 568/438; 203/91; 210/702; 210/737; 568/432
[58] Field of Search ................... 203/34–38, 91, 203/95–96, 92; 568/432, 438; 210/702, 723, 724, 737, 767

[56] References Cited

U.S. PATENT DOCUMENTS

| 4,435,601 | 3/1984 | Formanek et al. | 568/430 |
| 4,748,278 | 5/1988 | Röhrscheid | 568/438 |
| 4,772,754 | 9/1988 | Röhrscheid | 568/438 |

FOREIGN PATENT DOCUMENTS

| 0012939 | 7/1980 | European Pat. Off. . |
| 0209798 | 1/1987 | European Pat. Off. . |
| 0330036 | 8/1989 | European Pat. Off. . |
| 9200968 | 1/1994 | Netherlands . |

OTHER PUBLICATIONS

Chemical Abstracts, vol. 113, No. 17, abstract No. 152027d, abstract of JP 02–172,942, (1990).

Chemical Abstracts, vol. 110, No. 3, abstract No. 23536h, abstract of JP 63–216,839, (1988).

Chemical Abstracts, vol. 120, No. 11, abstract No. 134031r, abstract of NL 9200968, (1994).

Chemical Abstracts, vol. 112, No. 17, abstract No. 157866r, abstract of EP 330 036, (1989).

Chemical Abstracts, vol. 111, No. 21, abstract No. 194299h, abstract of JP 01–106,838, (1989).

Chemical Abstracts, vol. 113, No. 15, abstract No. 131746x, abstract of JP 02–172,941, (1990).

*Primary Examiner*—Virginia Manoharan
*Attorney, Agent, or Firm*—Sprung Kramer Schaefer & Briscoe

[57] ABSTRACT

A process for separating off poorly soluble by-products from reaction mixtures which are produced in the oxidation of p-cresol with oxygen or an oxygen-containing gas in methanol as solvent in the presence of alkali metal hydroxide and in the presence of metal compounds as catalyst, is characterized in that, after the oxidation, excess alkali is neutralized to the extent that a salt precipitate forms and this salt precipitate is separated off together with the poorly soluble by-products.

11 Claims, No Drawings

PROCESS FOR THE RECOVERY OF 4-HYDROXYBENZALDEHYDE FROM REACTION MIXTURES CONTAINING SAME

The present invention relates to a process for the purification of reaction mixtures containing 4-hydroxybenzaldehyde as are produced in the direct oxidation of p-cresol with oxygen.

BACKGROUND OF THE INVENTION

4-Hydroxybenzaldehyde is an important intermediate for the cinnamic esters used in cosmetics as UV absorbers. In addition, 4-hydroxybenzaldehyde is important for the synthesis of aroma substances, pharmaceuticals and plant protection products.

In the most expedient process at present for the preparation of 4-hydroxybenzaldehyde, p-cresol is oxidized with oxygen or an oxygen-containing gas in methanolic alkali and in the presence of metal compounds as catalysts. Suitable metal compounds are, for example, cobalt compounds (see EP-A 12 939), iron chelate complexes and/or manganese chelate complexes (see EP-A 330 036) and alumina-/silica- and/or phosphorus oxide-based microporous solids modified by cobalt, chromium or vanadium (see NL-A 92-968).

After the oxidation, 4-hydroxybenzaldehyde is present as an alkali metal salt dissolved in the methanolic alkaline reaction mixture. The reaction mixture is contaminated by poorly soluble resinous by-products. These by-products impair the quality of the isolated 4-hydroxybenzaldehyde and require addition purification steps. In addition, they make the work-up of the reaction mixture more difficult, because they promote emulsion formation between the water phase and organic phase, retard the crystallization of 4-hydroxybenzaldehyde and its salts and lead to the formation of very fine, and thus difficult to filter, crystals of 4-hydroxybenzaldehyde and its salts. Moreover, because of the resinous consistency of the by-products, caking and sticking to apparatus components occur, especially if it is not desired to isolate 4-hydroxybenzaldehyde but to react it further in the form of the reaction mixture, e.g. with methyl chloride to give anisaldehyde.

It is therefore expedient in all cases to remove these resinous by-products from the reaction mixture.

For reaction mixtures from the oxidation of p-cresol catalysed by cobalt compounds, it is known to obtain the 4-hydroxybenzaldehyde by crystallization of the sodium salt from aqueous alkali, separation of the sodium salt and liberation of 4-hydroxybenzaldehyde after redissolving (see JP-A2-02-172941 and JP-A2-63-216839).

In the work-up via the crystallization of the sodium salt, the by-products are separated off via the mother liquor. The by-products are highly soluble in aqueous alkali, but only sparingly soluble in methanolic alkali.

Isolation and purification of 4-hydroxybenzaldehyde via the sodium salt is associated with losses of yield due to portions in the mother liquor, is expensive in terms of apparatus and is thus cost-intensive.

It is also known to isolate 4-hydroxybenzaldehyde by distillation (see JP-A2-01-106838). This method is unsuitable for carrying out the procedure on an industrial scale because of the low thermal stability of crude 4-hydroxybenzaldehyde.

Direct filtration of the sparingly soluble by-products from the reaction mixture—a possibility which appears obvious—is described in combination with a downstream crystallization of the sodium salt of 4-hydroxybenzaldehyde (see JP-A2-02-172942). However, this direct filtration is unfavourable under operating circumstances, since the by-products to be separated off are present in a slimy, highly voluminous form with high contents of 4-hydroxybenzaldehyde and solvents. The filtration is therefore very lengthy (see present Example 5), washing the poorly soluble by-products filtered off is difficult because of the slimy consistency and is associated with considerable additional requirements of washing agent.

SUMMARY OF THE INVENTION

A process has now been found for separating off poorly soluble by-products from reaction mixtures which are produced in the oxidation of p-cresol with oxygen or an oxygen-containing gas in methanol as solvent in the presence of alkali metal hydroxide and in the presence of metal compounds as catalyst, which is characterized in that, after the oxidation, excess alkali is neutralized to the extent that a salt precipitate forms and this salt precipitate is separated off together with the poorly soluble by-products.

DETAILED DESCRIPTION

The excess alkali can be neutralized by addition of acid. If appropriate, the mixture may be additionally diluted with water.

In the oxidation of p-cresol, the alkali metal hydroxide preferably used is sodium hydroxide or potassium hydroxide, in particular sodium hydroxide. Based on p-cresol, for example, 2 to 6 molar equivalents of alkali metal hydroxide can be used. Preferably, this amount is 2.5 to 4.5 molar equivalents.

The methanol can be used in pure form or in a mixture with other solvents, e.g. with other alcohols such as ethylene glycol and/or tert-butanol and/or in a mixture with water. Preferably, the content of other solvents is less than 10% by weight, based on methanol.

The temperature in the oxidation of p-cresol can be between, e.g., 40° and 90° C., preferably the temperatures are between 45° and 85° C.

The pressure of the oxygen or of the oxygen-containing gas is subject to no particular restriction and can be, e.g., between 1 and 50 bar. Preferably, it is 1 to 10 bar. The oxygen content in the event of the use of oxygen-containing gases is likewise not subject to any restriction. The most economically expedient form is the use of atmospheric air.

The catalysts which can be used are, e.g., compounds of the transition metals, e.g. compounds of vanadium, chromium, manganese, iron, cobalt, copper and/or cerium. The compounds can be, e.g., oxides, hydroxides and/or salts of inorganic acids, for example fluorides, chlorides, sulphates, nitrates, carbonates and/or phosphates and/or salts of organic acids, for example acetates, oxalates, phenolates, benzoates and/or salicylates and/or complexes of these metals, for example with acetylacetone, N,N'-disalicylidenemethylenediamine, tetraarylporphyrines and/or phthalocyanines and/or solids of microporous structure modified by these metals, e.g. thus modified zeolites. Those which are preferably used are compounds of cobalt, e.g. in the form of the said metal salts and metal complexes, iron chelate complexes and/or manganese chelate complexes, in particular iron tetraarylporphyrines porphines and/or manganese tetraarylporphyrines and/or alumina-, silica- and/or phosphorus oxide-based solids of microporous structure modified by cobalt. Those which are particularly preferred are iron tetraarylporphyrines, if appropriate in combination with one or more copper compounds as cocatalysts.

Individual examples of iron tetraarylporphyrines which may be used are iron complexes of tetraphenylporphyrine, tetrakis-(4-methoxyphenyl)-porphyrine, tetrakis-(2-methoxyphenyl)-porphyrine, tetrakis-(2-chlorophenyl)-porphyrine, tetrakis-(2-hydroxyphenyl)-porphyrine and tetrakis-(2,4-dimethoxyphenyl)-porphyrine.

The molar ratio of catalyst, calculated as metal, to p-cresol used can be, e.g., 0.00001 to 0.05. Preferably, it is 0.0001 to 0.005.

The oxidation is preferably carried out to complete conversion of the p-cresol. However, according to the invention, reaction mixtures can also be worked up in which p-cresol has only been partially converted, and reaction mixtures which contain the incompletely oxidized intermediates 4-hydroxybenzyl alcohol and/or 4-hydroxybenzyl methyl ether.

Acids which are suitable for producing the salt precipitate are the most diverse strong and weak acids, e.g. hydrochloric acid, sulphuric acid, phosphoric acid, nitric acid, carbonic acid and acetic acid. The acids can be used individually or in any mixtures. Preferably, hydrochloric acid or sulphuric acid is used.

The acids can be used, e.g., in pure form or as aqueous solutions. The water content of such aqueous solutions can be varied in a broad range. It is only subject to the restriction that the entrained water does not completely dissolve the salt. Preference is given to the use of anhydrous acids or concentrated aqueous solutions of these acids, e.g. 10 to 35% strength by weight hydrochloric acid and 70 to 90% strength by weight sulphuric acid. The temperature of the reaction mixture can vary during the addition of acid, e.g. between 20° C. and the boiling temperature of the reaction medium. The temperature is generally chosen so that salt precipitates which may be readily separated off are produced. In the case of sodium sulphate, the coarsely crystalline $Na_2SO_4$ -10 $H_2O$ is preferentially precipitated. Good results are generally achieved at temperatures between 20° and 75° C.

The alkali excess present in the reaction mixture after the oxidation, which can be, depending on the procedure, e.g. 1 to 6 molar equivalents, preferably 1.5 to 4 molar equivalents, can, according to the invention, be neutralized completely, i.e. until a pH of approximately 10 is achieved, or only partially. Generally, at least 0.3 mol of alkali is neutralized per mole of p-cresol used for the oxidation. To what extent the neutralization must be taken in order to achieve optimal separation of the poorly soluble by-products together with the salt precipitate depends, inter alia, on the water content in the reaction mixture, on the type of salt and on the amount of the by-products and can readily be determined in an individual case by simple, routine preliminary tests.

The precipitate formed according to the invention of salt and poorly soluble by-products can be separated off by processes known per se for solids separation, e.g. by filtration or sedimentation. Suitable apparatuses therefor are, for example, pressure filters, belt filters, filter candles and centrifuges.

Surprisingly, by means of the salt precipitation according to the invention, the by-products which were previously difficult to separate off and poorly soluble may be very readily separated off from the reaction solution. Because of the known low adsorption capacity of inorganic salts, it was not predictable that the poorly soluble by-products can be virtually completely bound by the salt precipitate and by this means brought into an excellently separable form.

After the salt precipitate has been separated off together with the poorly soluble by-products, p-hydroxybenzaldehyde can be isolated free of resin and in high purity from the methanolic filtrate. The solutions freed of salt precipitate and the poorly soluble by-products are particularly suitable for the direct and thus inexpensive further processing to give secondary products of 4-hydroxybenzaldehyde. A cost-intensive intermediate isolation of 4-hydroxybenzaldehyde or its alkali metal salts for purification purposes can thus frequently be dispensed with. Problems with downstream work-up operations, for example in phase separations and crystallizations, no longer occur. Examples of secondary products which may advantageously be prepared by direct further processing of the reaction solutions freed of the salt precipitate and the poorly soluble by-products are anisaldehyde, 4-hydroxybenzonitrile and the aroma substance 1-(4-hydroxyphenyl)-3-butanone.

EXAMPLES

Percentages relate to the weight, unless otherwise stated.

Example 1

300 g of p-cresol (99% pure), 0.10 g of iron tetrakis-(2, 4-dimethoxyphenyl)-porphyrine chloride, 0.15 g of $Cu(NO_3)_2$ -3 $H_2O$, 1500 g of methanol and 417 g of sodium hydroxide were introduced sequentially into a 3 l glass reactor having a stirrer, reflux condenser and gas introduction tube. The starting mixture was heated to a temperature of 55° C. under a nitrogen atmosphere and stirred at this temperature for 90 minutes. A homogeneous dark green solution formed. A constant stream of 40 l of air/h was then introduced into this with vigorous stirring. The oxygen content in the off-gas established itself initially at about 6% by volume. After 16 hours the reaction was complete. The weight of the reaction mixture was then 2257 g and it contained, according to HPLC analysis, no p-cresol, 13.7% 4-hydroxybenzaldehyde and 0.2% 4-hydroxybenzoic acid.

220 ml of aqueous 80% strength sulphuric acid were then added dropwise at a temperature of 45° to 50° C. The pH was then 11. The salt precipitate containing essentially sodium sulphate and poorly soluble by-products was filtered off via a pressure filter (diameter 10 cm) at 2.5 bar gauge pressure. Filtration duration: 18 minutes. The filtrate was a clear, reddish solution.

Example 2

The oxidation was carried out as in Example 1. After the oxidation was completed, 550 ml of concentrated aqueous hydrochloric acid were added dropwise to the reaction mixture at a temperature of 60° to 65° C. The pH was then 11. The precipitate was filtered off as in Example 1. Filtration duration: 5 minutes.

Example 3

The oxidation was carried out as in Example 1. After the oxidation was completed, 110 ml of 80% strength aqueous sulphuric acid were added dropwise to the reaction mixture. The precipitate was filtered off as in Example 1. Filtration duration: 15 minutes.

Example 4

The oxidation was carried out as in Example 1. After the oxidation was completed, 55 ml of 80% strength aqueous sulphuric acid were added dropwise to the reaction mixture. The precipitate was filtered off as in Example 1. Filtration duration: 22 minutes.

Example 5 (Comparison Example—Filtration without prior addition of acid)

The oxidation was carried out as in Example 1. The reaction mixture was then filtered without prior addition of acid. Filtration duration: 260 minutes. The filtration residue essentially comprised poorly soluble by-products.

Example 6 (Isolation of 4-hydroxybenzaldehyde)

1000 g of the filtrate from Example 1 having a content of 13.9% 4-hydroxybenzaldehyde in the form of the sodium salt were subjected to exchange of methanol for water by distillation. The amount of water added was such that the volume of the aqueous solution after complete methanol distillation was 770 ml. 4-Hydroxybenzaldehyde was liberated from this solution at 50° C. by acidification with 80% strength aqueous sulphuric acid to a pH of 5.5. After the suspension was cooled to 20° C., 4-hydroxybenzaldehyde was filtered off, rinsed with 150 ml of water and dried. The yield was 135.4 g, the content was 99.1% (according to HPLC).

Example 7 (Further processing of the filtrate from Example 1 to give anisaldehyde)

1000 g of the filtrate from Example 1 having a content of 13.9% 4-hydroxybenzaldehyde in the form of the sodium salt were treated with 100 g of methyl chloride in a 2 l stainless steel autoclave at 95° C. and 6 bar. The pH in the reaction mixture was followed via a pH pressure electrode and kept between 8.5 and 8.7 by supplementary addition of 45% strength aqueous sodium hydroxide solution. After a reaction time of 8 hours, the pressure had fallen to 2.5 bar. The reaction mixture was cooled to room temperature, the methanol was distilled off with the addition of 1 g of potassium carbonate and the residue was diluted with 350 ml of water to dissolve the salts. The subsequent phase separation between the aqueous salt solution and the anisaldehyde phase proceeded without problem. The anisaldehyde phase was washed with 50 ml of water and then distilled at 20 mbar. Main fraction: 143.7 g having a content of 99.2% anisaldehyde.

What is claimed is:

1. In a process for the production of 4-hydroxybenzaldehyde from methanolic reaction mixture, wherein p-cresol is oxidized with oxygen or an oxygen containing gas in methanol as solvent and in the presence of sodium hydroxide or potassium hydroxide to form a reaction product comprising 4-hydroxybenzaldehyde and by-products, the improvement which comprises recovering the 4-hydroxybenzaldehyde from said reaction product by the steps of 1. neutralizing excess sodium or potassium hydroxide to an extent sufficient to form a salt precipitate from the methanolic reaction mixture consisting essentially of a member of the group consisting of sodium chloride, sodium sulphate, sodium phosphate, sodium nitrate, sodium carbonate, sodium acetate, potassium chloride, potassium sulphate, potassium phosphate, potassium nitrate, potassium carbonate, potassium acetate and combinations thereof, to which by-product impurities are bound, 2. separating said salt precipitate from said reaction product, thereby separating by-product impurities from said reaction product as well, and then 3. isolating the 4-hydroxybenzaldehyde from said reaction product.

2. The process of claim 1, in which the neutralization of the excess sodium or potassium hydroxide is carried out by addition of acid.

3. The process of claim 1, in which water is added in the neutralization.

4. The process of claim 1, in which at least 0.3 mol of the excess sodium or potassium hydroxide is neutralized per mole of p-cresol used for the oxidation.

5. The process of claim 1, in which the neutralization is performed with using a member of the group consisting of hydrochloric acid, sulphuric acid, phosphoric acid, nitric acid, carbonic acid, acetic acid and combinations of two or more of such members.

6. The process of claim 1, in which aqueous 10 to 35% strength by weight hydrochloric acid is used for neutralizing.

7. The process of claim 1, in which aqueous 70 to 90% strength by weight sulphuric acid is used for neutralizing.

8. The process of claim 1, wherein the oxidation is carried out in the presence of a catalyst selected from the group consisting of cobalt metal complexes, iron chelate complexes, manganese chelate complexes, and alumina, silica and phosphorus oxide-based solids of microporous structure modified by cobalt and combinations of two or more of such members.

9. The process of claim 8, wherein the iron chelate complex is an iron tetraarylporphyrine and the manganese chelate complex is a manganese tetraarylporphyrine.

10. The process of claim 9, wherein the chelate complex used is the iron tetraarylporphyrine.

11. The process of claim 8 in which the chelate complex is an iron tetraarylporphyrine in combination with at least one compound of copper.

* * * * *